US008877480B2

(12) United States Patent
Harman

(10) Patent No.: US 8,877,480 B2
(45) Date of Patent: Nov. 4, 2014

(54) TRICHODERMA STRAINS THAT INDUCE RESISTANCE TO PLANT DISEASES AND/OR INCREASE PLANT GROWTH

(71) Applicant: Gary E. Harman, Geneva, NY (US)

(72) Inventor: Gary E. Harman, Geneva, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/218,657

(22) Filed: Mar. 18, 2014

(65) Prior Publication Data

US 2014/0201869 A1    Jul. 17, 2014

Related U.S. Application Data

(62) Division of application No. 13/148,255, filed as application No. PCT/US2010/023453 on Feb. 8, 2010, now Pat. No. 8,716,001.

(60) Provisional application No. 61/150,567, filed on Feb. 6, 2009.

(51) Int. Cl.
*C12N 1/22* (2006.01)
*C12N 1/00* (2006.01)
*C12R 1/885* (2006.01)
*A01N 63/04* (2006.01)

(52) U.S. Cl.
CPC .............. *A01N 63/04* (2013.01); *C12R 1/885* (2013.01)
USPC ...................... 435/252; 435/254.1; 435/254.6

(58) Field of Classification Search
USPC .................................... 435/252, 254.1, 254.6
See application file for complete search history.

(56) References Cited

U.S. PATENT DOCUMENTS

| 4,489,161 A | 12/1984 | Papavizas |
| 4,642,131 A | 2/1987 | Hoitink |
| 4,668,512 A | 5/1987 | Lewis et al. |
| 4,678,669 A | 7/1987 | Ricard |
| 4,713,342 A | 12/1987 | Chet et al. |
| 4,748,021 A | 5/1988 | Chet et al. |
| 4,818,530 A | 4/1989 | Marois et al. |
| 4,828,600 A | 5/1989 | McCabe et al. |
| 4,837,155 A | 6/1989 | Tabachnik |
| 4,900,348 A | 2/1990 | Hoitink |
| 4,915,944 A | 4/1990 | Chet et al. |
| 5,068,105 A | 11/1991 | Lewis et al. |
| 5,071,462 A | 12/1991 | Kimura |
| 5,173,419 A | 12/1992 | Harman et al. |
| 5,192,686 A | 3/1993 | Ahmad et al. |
| 5,194,258 A | 3/1993 | Paau et al. |
| 5,204,260 A | 4/1993 | Ahmad et al. |
| 5,238,690 A | 8/1993 | Elad et al. |
| 5,260,213 A | 11/1993 | Harman et al. |
| 5,266,316 A | 11/1993 | Elad et al. |
| 5,273,749 A | 12/1993 | Bok et al. |
| 5,288,634 A | 2/1994 | Harman et al. |
| 5,330,912 A | 7/1994 | Toet et al. |
| 5,378,821 A | 1/1995 | Harman et al. |
| 5,422,107 A | 6/1995 | Kubota |
| 5,474,926 A | 12/1995 | Harman et al. |
| 5,628,144 A | 5/1997 | Eastin |
| 5,882,915 A | 3/1999 | Howell |
| 5,922,603 A | 7/1999 | Herrera-Estrella et al. |
| 5,981,844 A | 11/1999 | Roberts et al. |
| 6,060,507 A | 5/2000 | Hill et al. |
| 6,173,527 B1 | 1/2001 | Pryor |
| 6,242,420 B1 | 6/2001 | Hanson et al. |
| 6,444,437 B1 | 9/2002 | Sporleder et al. |
| 6,471,741 B1 | 10/2002 | Reinbergen |
| 6,475,772 B1 | 11/2002 | Kalra et al. |
| 6,512,166 B1 | 1/2003 | Harman et al. |
| 6,602,500 B1 | 8/2003 | Kharbanda et al. |
| 6,660,690 B2 | 12/2003 | Asrar et al. |
| 6,808,917 B1 | 10/2004 | Johnson |
| 6,838,473 B2 | 1/2005 | Asrar et al. |

(Continued)

FOREIGN PATENT DOCUMENTS

| EP | 0133878 B1 | 3/1990 |
| EP | 0383201 B1 | 5/1990 |

(Continued)

OTHER PUBLICATIONS

Marra et al. (Study of the three-way interaction between *Trichoderma atroviride*, plant and fungal pathogens by using a proteomic approach. Curr Genet (2006) 50:307-321).*
Extended European Search Report for European Patent Application No. 10739221.9-2405 (Mar. 29, 2012).
Sivan et al., "Improved Rhizosphere Competence in a Protoplast Fusion Progeny of *Trichoderma harzianum*," Journal of General Microbiology 137:23-29 (1991).
Stasz et al., "Nonparental Progeny Resulting from Protoplast Fusion in *Trichoderma* in the Absence of Parasexuality," Experimental Mycology 14:145-159 (1990).

(Continued)

*Primary Examiner* — Karen Cochrane Carlson
*Assistant Examiner* — Natalie Moss
(74) *Attorney, Agent, or Firm* — LeClairRyan, a Professional Corporation

(57) ABSTRACT

The present invention relates to a method for enhancing growth of plants which comprises contacting a *Trichoderma* strain with the plant or a plant seed under conditions effective for the *Trichoderma* strain to colonize the roots of the plant or a plant grown from the plant seed, thereby creating a plant-*Trichoderma* system. The plant or plant seed is grown under conditions effective to sustain the plant-*Trichoderma* system in a planting medium and to enhance plant growth, where the *Trichoderma* strain is selected from the group consisting of *Trichoderma atroviride* strain WW10TC4 (ATCC accession number PTA 9707), *Trichoderma harzianum* strain RR17Bc (ATCC accession number PTA 9708), *Trichoderma harzianum* strain F11Bab (ATCC accession number PTA 9709), and combinations thereof. Also, disclosed are methods of enhancing resistance of plants to abiotic stress, increasing nitrogen use efficacy in plants, reducing nitrous oxide emissions in air, reducing leaching of nitrates into soil and water, and enhancing sequestration of carbon from air.

20 Claims, 6 Drawing Sheets

(56) References Cited

U.S. PATENT DOCUMENTS

| | | |
|---|---|---|
| 6,890,530 B2 | 5/2005 | Hermosa Prieto et al. |
| 7,070,984 B2 | 7/2006 | Munoz |
| 7,273,552 B2 | 9/2007 | Lynch |
| 7,316,989 B2 | 1/2008 | Umemura et al. |
| 7,338,779 B1 | 3/2008 | Nakari-Setälä et al. |
| 7,374,786 B2 | 5/2008 | Hysmith |
| 7,422,737 B1 | 9/2008 | Nussinovitch et al. |
| 7,429,477 B2 | 9/2008 | Johnson |
| 7,553,657 B2 | 6/2009 | Gay et al. |
| 7,901,935 B2 | 3/2011 | Shukla et al. |
| 2002/0103083 A1 | 8/2002 | Harman et al. |
| 2002/0115564 A1 | 8/2002 | Asrar et al. |
| 2002/0115565 A1 | 8/2002 | Asrar et al. |
| 2002/0129406 A1 | 9/2002 | Asrar et al. |
| 2003/0092574 A1 | 5/2003 | Munoz |
| 2004/0048833 A1 | 3/2004 | Kohn |
| 2004/0121442 A1 | 6/2004 | Chet et al. |
| 2004/0151698 A1 | 8/2004 | Chung et al. |
| 2004/0176249 A1 | 9/2004 | Prieto et al. |
| 2004/0261578 A1 | 12/2004 | Harman et al. |
| 2004/0265953 A1 | 12/2004 | Dozeli et al. |
| 2005/0019767 A1 | 1/2005 | Shukla et al. |
| 2005/0096225 A1 | 5/2005 | Johnson |
| 2005/0124492 A1 | 6/2005 | Asrar et al. |
| 2005/0126990 A1 | 6/2005 | Lynch |
| 2005/0148470 A1 | 7/2005 | Asrar et al. |
| 2006/0292124 A1 | 12/2006 | Khan et al. |
| 2008/0254054 A1 | 10/2008 | Jackson et al. |
| 2008/0320615 A1 | 12/2008 | Johnson |
| 2009/0083819 A1 | 3/2009 | Robertson et al. |
| 2009/0104165 A1 | 4/2009 | Lorito et al. |
| 2009/0173001 A1 | 7/2009 | Ahm |
| 2009/0308121 A1 | 12/2009 | Reddy et al. |

FOREIGN PATENT DOCUMENTS

| | | |
|---|---|---|
| EP | 0470287 A1 | 2/1992 |
| EP | 0485229 B1 | 1/1995 |
| EP | 0544039 B1 | 6/1995 |
| EP | 0466133 B1 | 5/1997 |
| EP | 0586477 B1 | 8/1997 |
| EP | 0540713 B1 | 8/1998 |
| EP | 0670821 B1 | 11/2000 |
| EP | 1180523 A1 | 2/2002 |
| EP | 0949866 B1 | 5/2002 |
| EP | 1279335 A1 | 1/2003 |
| EP | 0492536 B1 | 5/2003 |
| EP | 1400586 A1 | 3/2004 |
| EP | 1279335 B1 | 4/2004 |
| EP | 1294850 B1 | 7/2004 |
| EP | 1481956 A1 | 12/2004 |
| EP | 0659215 B1 | 3/2005 |
| EP | 1322163 B1 | 3/2005 |
| EP | 1168922 B1 | 8/2005 |
| EP | 1204738 B1 | 1/2006 |
| EP | 1322166 B1 | 4/2007 |
| EP | 1322165 B1 | 5/2007 |
| EP | 1594952 B1 | 8/2007 |
| EP | 1844655 A2 | 10/2007 |
| EP | 1867724 A2 | 12/2007 |
| EP | 2009093 A2 | 12/2008 |
| EP | 1432738 B1 | 3/2009 |
| EP | 2062966 A1 | 5/2009 |
| EP | 1962572 B1 | 7/2009 |
| EP | 1400586 B1 | 11/2009 |
| EP | 1281753 B1 | 12/2009 |
| JP | 3192515 A | 8/1991 |
| JP | 3204719 A | 9/1991 |
| JP | 4029905 A | 1/1992 |
| JP | 6192028 A | 7/1994 |
| JP | 9087122 A | 3/1997 |
| JP | 10262460 A | 10/1998 |
| JP | 11279015 A | 10/1999 |
| WO | 8900375 A1 | 1/1989 |
| WO | 9107869 A1 | 6/1991 |
| WO | 9222314 A1 | 12/1992 |
| WO | 9301923 A1 | 2/1993 |
| WO | 9518859 A1 | 7/1995 |
| WO | 9520879 A2 | 8/1995 |
| WO | 9731879 A1 | 9/1997 |
| WO | 9741212 A1 | 11/1997 |
| WO | 9745018 A1 | 12/1997 |
| WO | 9945782 A1 | 9/1999 |
| WO | 9946208 A1 | 9/1999 |
| WO | 9963830 A1 | 12/1999 |
| WO | 0051435 A1 | 9/2000 |
| WO | 0075159 A1 | 12/2000 |
| WO | 0108490 A1 | 2/2001 |
| WO | 0183706 A1 | 11/2001 |
| WO | 0228186 A2 | 4/2002 |
| WO | 0230201 A2 | 4/2002 |
| WO | 0230202 A2 | 4/2002 |
| WO | 02065836 A2 | 8/2002 |
| WO | 02068666 A1 | 9/2002 |
| WO | 02087344 A1 | 11/2002 |
| WO | 02090492 A2 | 11/2002 |
| WO | 03020905 A2 | 3/2003 |
| WO | 03043411 A2 | 5/2003 |
| WO | 03045596 A1 | 6/2003 |
| WO | 2004054365 A2 | 7/2004 |
| WO | 2004089831 A2 | 10/2004 |
| WO | 2006036678 A2 | 4/2006 |
| WO | 2006065985 A2 | 6/2006 |
| WO | 2006121354 A1 | 11/2006 |
| WO | 2007065436 A1 | 6/2007 |
| WO | 2007/140256 A1 | 12/2007 |
| WO | 2007146944 A2 | 12/2007 |
| WO | 2008098933 A1 | 8/2008 |
| WO | 2008155514 A2 | 12/2008 |
| WO | 2009045023 A2 | 4/2009 |
| WO | 2009083819 A1 | 7/2009 |
| WO | 2009091557 A1 | 7/2009 |
| WO | 2009102222 A1 | 8/2009 |
| WO | 2009116106 A1 | 9/2009 |
| WO | 2009126473 A1 | 10/2009 |
| WO | 2009140315 A1 | 11/2009 |

OTHER PUBLICATIONS

Rao et al., "Evaluation of Plant Based Formulations of *Trichoderma harzianum* for the Management of Meloidogyne Incognita on Egg Plant," Nematol. Medit. 26:59-62 (1988).

Howell, "Mechanisms Employed by *Trichoderma* Species in the Biological Control of Plant Diseases: The History and Evolution of Current Concepts," Plant Dis. 87(1):4-10 (2003).

Harman et al., "*Trichoderma Species*—Opportunistic, Avirulent Plant Symbionts," Nat. Rev. Microbiol. 2:43-56 (2004).

PCT International Search Report and Written Opinion for PCT/US2010/023453, filed Feb. 8, 2010.

* cited by examiner

TRICHODERMA STRAINS THAT INDUCE RESISTANCE TO PLANT DISEASES AND/OR INCREASE PLANT GROWTH

This application is a divisional of U.S. patent application Ser. No. 13/148,255, which is a national stage application under 35 U.S.C. §371 of PCT Application No. PCT/US2010/023453, filed Feb. 8, 2010, which claims the benefit of U.S. Provisional Patent Application Ser. No. 61/150,567, filed Feb. 6, 2009, all of which are hereby incorporated by reference in their entirety.

This invention was made with government support under United States Department of Agriculture (USDA) grant numbers 2008-00169 and 2009-01133. The government has certain rights in this invention.

FIELD OF THE INVENTION

The present invention relates to *Trichoderma* strains that induce resistance to plant diseases and/or increase plant growth.

BACKGROUND OF THE INVENTION

*Trichoderma* spp. have been known as biocontrol agents since the 1930s (Weindling, R., "*Trichoderma lignorum* as a Parasite of Other Soil Fungi," *Phytopathology* 22:837-845 (1932)) and have been shown to have dramatic effects on plants (Chet, I., "Innovative Approaches to Plant Disease Control," In R. Mitchell (ed.), *Wiley Series in Ecological and Applied Microbiology* pp. 372. Jon Wiley & Sons, New York (1987); Harman, G., "Myths and Dogmas of Biocontrol. Changes in Perceptions Derived from Research on *Trichoderma harzianum* T-22," *Plant Dis.* 84:377-393 (2000)). The effects noted include (a) increased growth and yields of plants (Chang et al., "Increased Growth of Plants in the Presence of the Biological Control Agent *Trichoderma harzianum*," *Plant Dis.* 70:145-148 (1986); Harman, G., "Myths and Dogmas of Biocontrol. Changes in Perceptions Derived from Research on *Trichoderma harzianum* T-22," *Plant Dis.* 84:377-393 (2000); Lindsey et al., "Effect of Certain Fungi on Dwarf Tomatoes Grown under Gnotobiotic Conditions," *Phytopathology* 57:1262-1263 (1967); Yedidia et al., "Effect of *Trichoderma harzianum* on Microelement Concentrations and Increased Growth of Cucumber Plants," *Plant Soil* 235:235-242 (2001)); (b) increased root growth and drought tolerance (Harman, G., "Myths and Dogmas of Biocontrol. Changes in Perceptions Derived from Research on *Trichoderma harzianum* T-22," *Plant Dis.* 84:377-393 (2000)); (c) induced systemic resistance to disease (Geremia et al., "Molecular Characterization of the Proteinase-Encoding Gene, Prb1, Related to Mycoparasitism by *Trichoderma harzianum*," *Molec. Microbiol.* 8:603-613 (1993); Harman et al., "*Trichoderma* Species—Opportunistic, Avirulent Plant Symbionts," *Nature Rev. Microbiol.* 2:43-56 (2004); Yedidia et al., "Induction of Defense Responses in Cucumber Plants (*Cucumis sativus* L.) by the Biocontrol Agent *Trichoderma harzianum*," *Appl. Environ. Microbiol.* 65:1061-1070 (1999); Yedidia et al., "Induction and Accumulation of PR Proteins Activity During Early Stages of Root Colonization by the Mycoparasite *Trichoderma harzianum* Strain T-203," *Plant Physiol. Biochem.* 38:863-873 (2000); Yedidia et al., "Concomitant Induction of Systemic Resistance to *Pseudomonas syringae* pv. *Lachrymans* in Cucumber by *Trichoderma asperellum* (T-203) and Accumulation of Phytoalexins," *Appl. Environ. Microbiol.* 69:7343-7353 (2003)); (d) increased nutrient uptake and fertilizer utilization efficiency (Harman, G., "Myths and Dogmas of Biocontrol. Changes in Perceptions Derived from Research on *Trichoderma harzianum* T-22," *Plant Dis.* 84:377-393 (2000); Yedidia et al., "Effect of *Trichoderma harzianum* on Microelement Concentrations and Increased Growth of Cucumber Plants," *Plant Soil* 235:235-242 (2001)); (e) increased leaf greenness, increased expression of proteins involved in photosynthesis and greater starch accumulation that is indicative of increased photosynthetic rate (Harman, G., "Myths and Dogmas of Biocontrol. Changes in Perceptions Derived from Research on *Trichoderma harzianum* T-22," *Plant Dis.* 84:377-393 (2000); Harman et al., "The Mechanisms and Applications of Opportunistic Plant Symbionts," In M. Vurro and J. Gressel (eds.), *Novel Biotechnologies for Biocontrol Agent Enhancement and Management* pp. 131-153. Springer, Amsterdam (2007)); and (f) increased percentages of germination and rates of germination of seeds (Bjorkman et al., "Growth Enhancement of Shrunken-2 Sweet Corn with *Trichoderma harzianum* 1295-22: Effect of Environmental Stress," *J. Am. Soc. Hort. Sci.* 123:35-40 (1998); Chang et al., "Increased Growth of Plants in the Presence of the Biological Control Agent *Trichoderma harzianum*," *Plant Dis.* 70:145-148 (1986)). In addition, *Trichoderma* strains alleviated effects of salt stress on squash plant growth (Yildirim et al., "Ameliorative Effects of Biological Treatments on the Growth of Squash Plants Under Salt Stress," *Sci. Hortic.* 111:1-6 (2006)) and can overcome the negative effects of low levels of osmotic stress on germination of tomato seeds. *Trichoderma* strains can alleviate not only stresses extrinsic to plants, but also intrinsic stresses. Seeds lose vigor as they age but seed treatments with *Trichoderma* spp. can restore vigor and improve germination, even in the presence of any pathogenic organisms (Bjorkman et al., "Growth Enhancement of Shrunken-2 Sweet Corn with *Trichoderma harzianum* 1295-22: Effect of Environmental Stress," *J. Am. Soc. Hort. Sci.* 123:35-40 (1998)).

This long list of effects indicates that the *Trichoderma*-plant interactions are complex. They must involve alterations in a wide range of plant metabolic pathways and, almost by definition, widespread changes in gene expression and in the physiology of plants. This indicates that *Trichoderma* can essentially re-program plant genes and protein expression, and generally this results in benefits to plant growth and productivity and in resistance to biotic and abiotic stresses, including those that occur intrinsically, such as via seed aging. This capability of a fungus to re-program a maize plant is not without precedent—the maize smut pathogen also has this ability (Doehlemann et al., "Reprogramming a Maize Plant: Transcriptional and Metabolic Changes Induced by the Fungal Biotroph *Ustilago maydis*," *Plant J.* 56:181-95 (2008)).

Since 2000, the international *Trichoderma* research community, especially with the availability of "-omics" tools, has been able to arrive at a consensus as to the events that occur in the *Trichoderma*-plant interaction. Harman et al., "*Trichoderma* Species—Opportunistic, Avirulent Plant Symbionts," *Nature Rev. Microbiol.* 2:43-56 (2004)) provides a complete review of such interactions. These *Trichoderma*-plant interactions can be summarized as follows: (a) *Trichoderma* strains colonize and infect the outer layers of roots (Yedidia et al., "Induction of Defense Responses in Cucumber Plants (*Cucumis sativus* L.) by the Biocontrol Agent *Trichoderma harzianum*," *Appl. Environ. Microbiol.* 65:1061-1070 (1999); Yedidia et al., "Induction and Accumulation of PR Proteins Activity During Early Stages of Root Colonization by the Mycoparasite *Trichoderma harzianum* Strain T-203," *Plant Physiol. Biochem.* 38:863-873 (2000)); (b) once infection occurs, a zone of chemical interaction develops at these sites. Within this zone of chemical interaction, the *Trichoderma* hyphae are walled off by the plant but are not killed (Harman et al., "*Trichoderma* Species—Opportunistic, Avirulent Plant Symbionts," *Nature Rev. Microbiol.* 2:43-56 (2004); Harman et al., "The Mechanisms and Applications of Opportunistic Plant Symbionts," In M. Vurro and J. Gressel (eds.), *Novel Biotechnologies for Biocontrol Agent Enhancement and Management* pp. 131-153. Springer, Amsterdam (2007)). This walling off is accomplished through the interaction of chemical elicitors from *Trichoderma* with plant receptors. Some of the elicitors now are known and the hypothesis that *Trichoderma* spp. induce wide-scale changes in the physiology of the plant holds true and has been verified by both proteomic and transcriptomic assays (Alfano et al., "Systemic Modulation of Gene Expression in Tomato by *Trichoderma harzianum* 382," *Phytopathology* 97:429-437 (2007); Bailey et al., "Fungal and Plant Gene Expression During the Colonization of Cacao Seedlings by Endophytic Isolates of Four *Trichoderma* Species," *Planta (Berlin)* 224:1449-1464 (2006); Djonovic et al., "Sm1, a Proteinaceous Elicitor Secreted by the Biocontrol Fungus *Trichoderma virens* Induces Plant Defense Responses and Systemic Resistance," *Molec. Plant Microbe Interact.* 8:838-853 (2006); Djonovic et al., "A Proteinaceous Elicitor Sm1 from the Beneficial Fungus *Trichoderma virens* is Required for Systemic Resistance in Maize," *Plant Physiol.* 145:875-889 (2007); Marra et al., "Biocontrol Interactions Involving Plants, Fungal Pathogens and Antagonists of the Genus *Trichoderma*," *Abstracts, XIII International Congress on Molecular Plant-Microbe Interactions:* 399 (2007); Segarra et al., "Proteome, Salicylic Acid and Jasmonic Acid Changes in Cucumber Plants Inoculated with *Trichoderma asperellum* Strain T34," *Proteomics* 7:3943-3952 (2007); Shoresh et al., "Characterization of a Mitogen-Activated Protein Kinase Gene from Cucumber Required for *Trichoderma*-Conferred Plant Resistance," *Plant Physiol.* 142:1169-1179 (2006); Shoresh et al., "Genome-Wide Identification, Expression and Chromosomal Location of the Chitinase Genes in *Zea mays*," *Molec. Gen. Genom.* 280:173-85 (2008); Viterbo et al., "The 18mer Peptaibols from *Trichoderma virens* Elicit Plant Defence Responses," *Molec. Plant Pathol.* 8:737-746 (2007); Yedidia et al., "Induction and Accumulation of PR Proteins Activity During Early Stages of Root Colonization by the Mycoparasite *Trichoderma harzianum* Strain T-203," *Plant Physiol. Biochem.* 38:863-873 (2000); Yedidia et al., "Concomitant Induction of Systemic Resistance to *Pseudomonas syringae* pv. *Lachrymans* in Cucumber by *Trichoderma asperellum* (T-203) and Accumulation of Phytoalexins," *Appl. Environ. Microbiol.* 69:7343-7353 (2003)).

While the references cited represent major steps forward in the understanding of plant-*Trichoderma* interactions, it is just a beginning in an effort to elucidate the mechanisms and systems involved in this important plant-microbe symbiosis. An important fact is that strains differ substantially in their effects on plants. Only a few effectively enhance plant growth, induce high levels of systemic disease or stress resistance and provide the other advantages noted above. In large part, this is probably due to the fact that different strains produce different elicitors. Changes in gene expression can be used to formulate hypotheses regarding physiological changes in plants. For example, based on proteomic data, it can be hypothesized that *T. harzianum* strain T22 increases photosynthetic rates, respiration rates, and induces resistance to biotic and abiotic stresses.

It is worth noting that, while T22 has been widely used, other nonrhizosphere competent strains have largely fallen by the wayside, such as the strain described in Lumsden et al., "Isolation and Localization of the Antibiotic Gliotoxin Produced by *Gliocladium virens* from Alginate Prill in Soil and Soilless Media," *Phytopathology* 82:230-235 (1992). This strain produces the antibiotic gliotoxin and protects plants for a few weeks. After that time, this strain, which is not rhizosphere competent, becomes quiescent and its activity is lost.

The interaction of *Trichoderma* strains with plants may increase the nitrogen use efficiency. Globally the nitrogen (N) problem is a big one. About 60 percent of streams sampled in the U.S. show some signs of excess nitrogen loading. The World Water Council, an independent association of water scientists and engineers, reported that more than half of the world's biggest fresh-water lakes are threatened by pollution or drainage schemes. Coastal ecosystems are also affected. The Gulf of Mexico, for example, contains a notorious oxygen-depleted "dead zone" caused by agricultural run-off from the Mississippi river. One study on the Mississippi River basin found that reducing fertilizer use by just 12 percent would reduce nitrogen runoff by 33 percent (McIsaac et al., "Nitrate Flux in the Mississippi River," *Nature* 414:166-167 (2001)). This may occur because anthroprogenic nitrogen application exceeds the capacity of terrestrial or aquatic systems to assimilate nitrogen input.

Further, three gases associated with agriculture—nitrous oxide ($N_2O$), methane, and carbon dioxide—contribute to the level of greenhouse gases that are largely responsible for global warming. $N_2O$ is released from soils and its greenhouse warming potential (GWP) is 296 times greater than that of $CO_2$ (Snyder, C., "Fertilizer Nitrogen BMPs to Limit Losses that Contribute to Global Warming," International Plant Nutrition Institute, Norcross, Ga. (2008)). Best Management Practices can reduce $N_2O$ emissions by proper placement and application of nitrogen fertilizer. In particular, avoidance of over application, avoidance of application to saturated soils and application when plants are ready to immediately take up fertilizer can minimize excess nitrogen applications that result in elevated levels of $NO_3$—N in the soil profile. $NO_3$—N is readily converted to volatile $N_2O$ through the activities of soil microbes. The amount of $N_2O$ evolved from soil-applied nitrogen fertilizer is not trivial. In Canada alone, 9.2 megatonnes were estimated to be released (Art Jaques, P. EngChief—GHG Division, Environment, Canada) and the amounts released in the USA and other major agricultural countries would be expected to be much larger.

The present invention is directed to overcoming the deficiencies in the art.

SUMMARY OF THE INVENTION

In one aspect, the present invention relates to a method for enhancing growth of plants which comprises contacting a *Trichoderma* strain with the plant or a plant seed under conditions effective for the *Trichoderma* strain to colonize the roots of the plant or a plant grown from the plant seed, thereby creating a plant-*Trichoderma* system. The plant or plant seed is grown under conditions effective to sustain the plant-*Trichoderma* system in a planting medium and to enhance plant growth, wherein the *Trichoderma* strain is selected from the group consisting of *Trichoderma atroviride* strain WW10TC4 (ATCC accession number PTA 9707), *Trichoderma harzianum* strain RR17Bc (ATCC accession number PTA 9708), *Trichoderma harzianum* strain F11Bab (ATCC accession number PTA 9709), and combinations thereof.

Another aspect the present invention relates to a method for enhancing resistance of plants to abiotic stresses which comprises contacting a *Trichoderma* strain with the plant or a plant seed under conditions effective for the *Trichoderma* strain to colonize the roots of the plant or a plant grown from the plant seed, thereby creating a plant-*Trichoderma* system. The plant or plant seed is grown under conditions effective to sustain the plant-*Trichoderma* system in a planting medium and to enhance resistance of plants to abiotic stresses, where the *Trichoderma* strain is selected from the group consisting of *Trichoderma atroviride* strain WW10TC4 (ATCC accession number PTA 9707), *Trichoderma harzianum* strain RR17Bc (ATCC accession number PTA 9708), *Trichoderma harzianum* strain F11Bab (ATCC accession number PTA 9709), and combinations thereof.

The present invention also relates to a method for increasing nitrogen use efficacy in plants which comprises contacting a *Trichoderma* strain with the plant or a plant seed under conditions effective for the *Trichoderma* strain to colonize the roots of the plant or a plant grown from the plant seed, thereby creating a plant-*Trichoderma* system. The plant or plant seed is grown under conditions effective to sustain the plant-*Trichoderma* system in a planting medium and to increase nitrogen use efficacy in plants, where the *Trichoderma* strain is selected from the group consisting of *Trichoderma atroviride* strain WW10TC4 (ATCC accession number PTA 9707), *Trichoderma harzianum* strain RR17Bc (ATCC accession number PTA 9708), *Trichoderma harzianum* strain F11Bab (ATCC accession number PTA 9709), and combinations thereof.

The present invention also relates to a method for reducing nitrous oxide emissions in air and leaching of nitrates into soil and water which comprises contacting a *Trichoderma* strain with the plant or a plant seed under conditions effective for the *Trichoderma* strain to colonize the roots of the plant or a plant grown from the plant seed, thereby creating a plant-*Trichoderma* system. The plant or plant seed is grown under conditions effective to sustain the plant-*Trichoderma* system in a planting medium and to reduce nitrous oxide emissions in air and leaching of nitrates into soil and water, where the *Trichoderma* strain is selected from the group consisting of *Trichoderma atroviride* strain WW10TC4 (ATCC accession number PTA 9707), *Trichoderma harzianum* strain RR17Bc (ATCC accession number PTA 9708), *Trichoderma harzianum* strain F11Bab (ATCC accession number PTA 9709), and combinations thereof.

The present invention further relates to a method for enhanced sequestration of carbon from air which comprises contacting a *Trichoderma* strain with the plant or a plant seed under conditions effective for the *Trichoderma* strain to colonize the roots of the plant or a plant grown from the plant seed, thereby creating a plant-*Trichoderma* system. The plant or plant seed is grown under conditions effective to sustain the plant-*Trichoderma* system in a planting medium and to enhance sequestration of carbon from air, where the *Trichoderma* strain is selected from the group consisting of *Trichoderma atroviride* strain WW10TC4 (ATCC accession number PTA 9707), *Trichoderma harzianum* strain RR17Bc (ATCC accession number PTA 9708), *Trichoderma harzianum* strain F11Bab (ATCC accession number PTA 9709), and combinations thereof.

In another aspect, the present invention is related to an isolated *Trichoderma atroviride* strain WW10TC4 deposited with American Type Culture Collection (ATCC) under accession number PTA 9707.

The present invention also relates to an isolated *Trichoderma harzianum* strain RR17Bc deposited with ATCC under accession number PTA 9708.

The present invention also relates to an isolated *Trichoderma harzianum* strain F11Bab deposited with ATCC under accession number PTA 9709.

The invention further relates to a plant-*Trichoderma* system which comprises of a plant or a plant seed and a *Trichoderma* strain selected from the group consisting of *Trichoderma atroviride* strain WW10TC4 (ATCC accession number PTA 9707), *Trichoderma harzianum* strain RR17Bc (ATCC accession number PTA 9708), *Trichoderma harzianum* strain F11Bab (ATCC accession number PTA 9709), and combinations thereof.

*Trichoderma* has been demonstrated to be opportunistic avirulent plant symbiont and form plant-*Trichoderma* system (Harman et al., "*Trichoderma* Species—Opportunistic, Avirulent Plant Symbionts," *Nature Microbiol Rev* 2:43-56, (2004), which is hereby incorporated by reference in its entirety). These fungi clearly are opportunistic, since they can proliferate, compete, and survive in soil and other complex ecosystems. They are capable of invading roots, but are typically restricted to the outer layers of the cortex (Yedidia et al., "Induction of Defense Responses in Cucumber Plants (*Cucumis sativus* L.) by the Biocontrol Agent *Trichoderma harzianum*," *Appl Environ Microbiol* 65:1061-1070 (1999), which is hereby incorporated by reference in its entirety), probably due to production by the fungi of several classes of compounds that act as signals for the plant to activate resistance responses based on chemical and structural mechanisms (Harman et al., "*Trichoderma* Species—Opportunistic, Avirulent Plant Symbionts," *Nature Microbiol Rev* 2:43-56 (2004), which is hereby incorporated by reference in its entirety). This root infection followed by limitation of fungal proliferation within the root allows the fungi to grow and to develop using the energy sources of the plant. Not only do the fungi grow based upon resources provided by the plant, but they also are carried through soil and occupy new soil niches as a consequence of root colonization. Thus, root-associated *Trichoderma* spp. derive numerous benefits from plants.

The present invention is directed to newly identified strains that enhance plant growth. The colonization by *Trichoderma* promotes the enhancement of plant growth and development, especially of roots. However, the lack of adverse effects and the ability to stimulate plant growth are not universal among *Trichoderma* spp. For example, Ousley et al. showed that some strains enhance growth of lettuce or flowering shoots, but that others can inhibit plant growth (Ousley et al., "Effect of *Trichoderma* on Plant Growth: A Balance Between Inhibition and Growth Promotion," *Microbial. Ecol.* 26:277-285 (1993); Ousley et al., "The Effects of Addition of *Trichoderma* Inocula on Flowering and Shoot Growth of Bedding Plants," *Sci. Hort. Amsterdam* 59:147-155 (1994), which are hereby incorporated by reference in their entirety).

The choice of strains is extremely important, because different strains have different effects on the plants. For example, nonrhizosphere competent strains remain in soil and on roots as quiescent spores, and they are ineffective as biocontrol agents in this dormant state (Lewis et al., "A New Approach to Stimulate Population Proliferation of *Trichoderma* Species and Other Potential Biocontrol Fungi Introduced into Natural Soils," *Phytopathology* 74:1240-44 (1984), which is hereby incorporated by reference in its entirety) Rhizosphere competence no doubt results from the fact that certain strains of *Trichoderma* become established as endophytic plant symbionts. Many *Trichoderma* strains colonize plant roots of both dicots and monocots (Harman et al., "The Mechanisms and Applications of Opportunistic Plant Symbionts," In M. Vurro and J. Gressel (eds.), Novel Biotechnologies for Biocontrol Agent Enhancement and Management, pp. 131-153. Springer, Amsterdam (2007), which is hereby incorporated by reference in its entirety). During this process *Trichoderma* hyphae coil around the roots, form appresoria-like structures and finally penetrate the root cortex (Yedidia et al., "Induction and Accumulation of PR Proteins Activity During Early Stages of Root Colonization by the Mycoparasite *Trichoderma harzianum* Strain T-203," *Plant Physiol. Biochem.* 38:863-873 (1999), which is hereby incorporated by reference in its entirety).

This fact that *Trichoderma* spp. added to soil increases plant growth and development seems counterintuitive since, no doubt, the root colonization and induction of resistance is energetically expensive to the plants, but it is a phenomenon that is commonly observed on a variety of plants. Some of this improved plant growth likely occurs as a consequence of control of pathogenic or other deleterious microbes, but it also has been demonstrated in axenic systems (Harman, G. E., "Myths and Dogmas of Biocontrol. Changes in Perceptions Derived From Research on *Trichoderma harzianum* T-22," *Plant Disease* 84, 377-393 (2000); Harman et al., "*Trichoderma* Species—Opportunistic, Avirulent Plant Symbionts," *Nature Microbiol Rev* 2:43-56, (2004), which are hereby incorporated by reference in their entirety), so it is no doubt a consequence of direct effects on plants as well as a biological control phenomenon (Harman et al, "Interactions Between *Trichoderma harzianum* Strain T22 and Maize Inbred Line Mo 17 and Effects of this Interaction on Diseases Caused by *Pythium ultimum* and *Colletotrichum graminicola*," *Phytopathology* 94:147-153 (2004), which is hereby incorporated by reference in its entirety).

Certain *Trichoderma* strains have previously been known to cause plants to become greener and to increase plant yields (Harman, G. E., "The Myths and Dogmas of Biocontrol. Changes in Perceptions Based on Research with *Trichoderma harzianum* T-22," *Plant Disease* 84:377-393 (2000), which is hereby incorporated by reference in its entirety). Root development of the plant is also enhanced upon *Trichoderma* colonization, resulting in a greater root mass and depth of rooting. Consequently, the level of thoroughness of root exploration of the soil is increased and soil spaces between roots is lessened. The combination of thoroughness of root exploration and greater root depth results in more efficient nutrient uptake from soil or water.

DETAILED DESCRIPTION OF THE INVENTION

Figure 1:
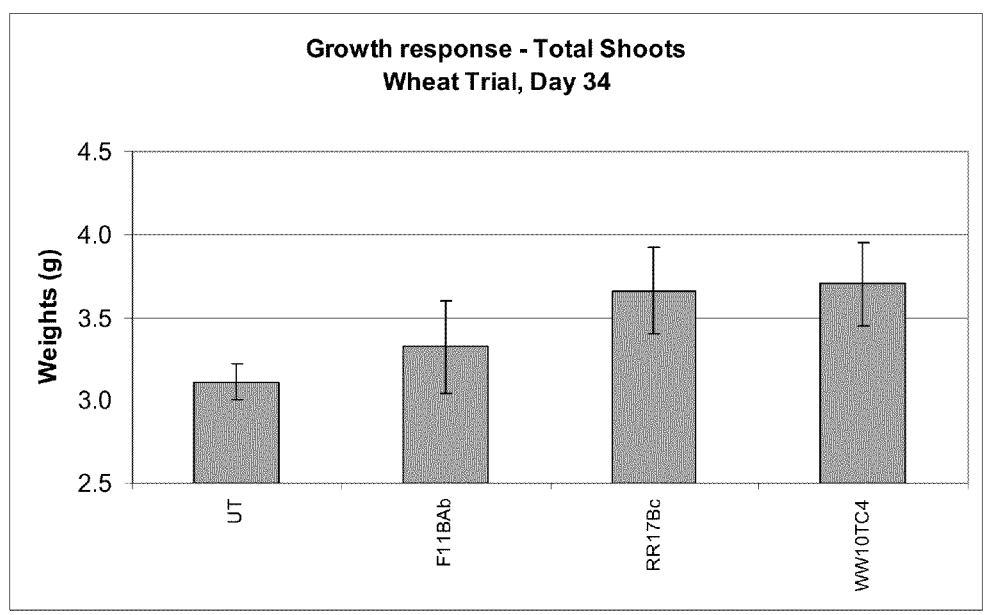
FIG. 1 shows the seedling sizes of wheat grown from seeds treated in accordance with the present invention.

The present invention relates to novel *Trichoderma* strains obtained by protoplast fusion. It relates to an isolated *Trichoderma atroviride* strain WW deposited with American Type Culture Collection (ATCC) under accession number PTA 9707, an isolated *Trichoderma harzianum* strain RR17Bc deposited with ATCC under accession number PTA 9708, and an isolated *Trichoderma harzianum* strain F11Bab deposited with ATCC under accession number PTA 9709. The isolated *Trichoderma* strains of the present invention can be in a biologically pure form.

The *Trichoderma* strains of the present invention can be produced in large quantities in-either liquid or semi-solid fermentation by routine microbial techniques, such as those described in Harman et al., "Potential and Existing Uses of *Trichoderma* and *Gliocladium* For Plant Disease Control and Plant Growth Enhancement," In *Trichoderma* and *Gliocladium*, Harman et al., eds., Vol. 2, London: Taylor and Francis (1998), which is hereby incorporated by reference in its entirety. Those skilled in the art will appreciate that the physiology and type of propagule (e.g., hyphae, conidia, or chlamydospores) of the source organism will dictate preparation schema and optimization of yield.

The invention also relates to a plant-*Trichoderma* system which comprises a plant or a plant seed and a *Trichoderma* strain selected from the group consisting of *Trichoderma atroviride* strain WW10TC4 (ATCC accession number PTA 9707), *Trichoderma harzianum* strain RR17Bc (ATCC accession number PTA 9708), *Trichoderma harzianum* strain F11Bab (ATCC accession number PTA 9709), and combinations thereof.

In one aspect, the present invention relates to a method for enhancing growth of plants which comprises contacting a *Trichoderma* strain with the plant or a plant seed under conditions effective for the *Trichoderma* strain to colonize the roots of the plant or a plant grown from the plant seed, thereby creating a plant-*Trichoderma* system. The plant or plant seed is grown under conditions effective to sustain the plant-*Trichoderma* system in a planting medium and to enhance plant growth, wherein the *Trichoderma* strain is selected from the group consisting of *Trichoderma atroviride* strain WW10TC4 (ATCC accession number PTA 9707), *Trichoderma harzianum* strain RR17Bc (ATCC accession number PTA 9708), *Trichoderma harzianum* strain F11Bab (ATCC accession number PTA 9709), and combinations thereof.

Without placing any limitations, plant growth may be in the form of greater root mass, greater depth of rooting, greater shoot mass, greater length of shoots, increased leaf greenness, increased yields, and improved stand and vigor. Plant growth can be established and ascertained by other means besides the extrinsic properties listed above. A person of skill in the art would readily be able to establish physical, biochemical or genetic assays to identify and/or quantify plant growth or viability. The methods of the present invention also describe ways of increasing the yield of crop plants. This involves contacting a crop plant or a crop plant seed and a symbiotic rhizosphere competent *Trichoderma* strain of the present invention capable of colonizing plant roots. *Trichoderma* can be combined with the crop plant or crop plant seed under conditions effective for the fungal organism to colonize the roots of the plant or a plant grown from the plant seed, thereby increasing the yield of the crop plant.

*Trichoderma* grows intercellularly in the root epidermis and cortex and induces the surrounding plant cells to deposit cell wall material and produce phenolic compounds. This plant reaction limit the *Trichoderma* growth inside the root (Yedidia et al., "Induction and Accumulation of PR Proteins Activity During Early Stages of Root Colonization by the Mycoparasite *Trichoderma harzianum* Strain T-203," *Plant Physiol. Biochem.* 38:863-873 (1999), which is hereby incorporated by reference in its entirety). Endophytic plant symbionts have much longer periods of efficacy since they have the ability to grow with plants and in the environment; therefore if conditions are favorable for them, they may have effects for weeks or months. These organisms may develop on or in plant roots and provide benefits to plants for at least the life of an annual crop (Harman, G. E., "Myths and Dogmas of biocontrol. Changes in Perceptions Derived from Research on *Trichoderma harzianum* T-22," *Plant Dis.* 84:377-393 (2000) and Harman et al., "Changing Paradigms on the Mode of Action and Uses of *Trichoderma* spp. for Biocontrol," *Outlooks Pest Manag.* 19:24-29 (2008), which are hereby incorporated by reference in their entirety). The establishment of living hyphae of the beneficial organisms in the root cortex results in chemical communication with the plant.

As a consequence, reprogramming of plant gene expression occurs, and numerous benefits to the plant result. This capability of growing on, or conidial germination on, root surfaces makes possible many kinds of application methods. These include, but are not limited to, seed treatments, application to soils or planting mixes as drenches that penetrate the soil volume and in-furrow application at the time of planting, broadcast or spray applications to soil surfaces containing roots. It also permits the use of very small amounts of inoculum (10s of g/ha) applied as a seed treatment, but that then results in subsequent proliferation of the organism on roots, causing season-long effects, including plant protection, greater root proliferation and enhanced exploration of the soil by roots (Adams et al., "*Trichoderma harzianum* Rifai 1295-22 Mediates Growth Promotion of Crack Willow (*Salix fragilis*) Saplings in Both Clean and Metal-contaminated Soil," *Microbial. Ecol.* 54:306-313 (2007); Harman, G. E., "Myths and Dogmas of Biocontrol. Changes in Perceptions Derived from Research on *Trichoderma harzianum* T-22," *Plant Dis.* 84:377-393 (2000); Harman et al., "Changing Paradigms on the Mode of Action and Uses of *Trichoderma* spp. for Biocontrol," *Outlooks Pest Manag.* 19:24-29 (2008); and Harman et al., "*Trichoderma* Species—Opportunistic, Avirulent Plant Symbionts," *Nature Rev. Microbiol.* 2:43-56 (2004), which are hereby incorporated by reference in their entirety).

*Trichoderma* strains suitable for the present invention are strains with strong abilities to colonize roots. This ability is known as rhizosphere competence, which is used herein to describe those organisms capable of colonizing the root surface or the surface plus surrounding soil volume (rhizoplane and rhizosphere, respectively), when applied as a seed or other point source at the time of planting in absence of bulk flow of water. Thus, the organisms of the present invention have the physiological and genetic ability to proliferate in and on the root as it develops. Rhizosphere competence is not an absolute term, and degrees of this ability may occur among strains (Harman, G. E., "The Development and Benefits of Rhizosphere Competent Fungi for Biological Control of Plant Pathogens," *J. Plant Nutrition* 15:835-843 (1992); U.S. Pat. Nos. 4,996,157 and 5,165,928 to Smith, which are hereby incorporated by reference in their entirety). Procedures for measuring rhizosphere competence are known to those skilled in the art (Harman et al., "Combining Effective Strains of *Trichoderma harzianum* and Solid Matrix Priming to Improve Biological Seed Treatments," *Plant Disease* 73:631-637 (1989); Harman, G. E., "The Myths and Dogmas of Biocontrol. Changes in Perceptions Based on Research with *Trichoderma harzianum* T-22," *Plant Disease* 84:377-393 (2000); Kloepper et al., "A Review of Issues Related to Measuring Colonization of Plant Roots by Bacteria," *Can J. Microbiol.* 38:1219-1232 (1992), which are hereby incorporated by reference in their entirety). For the purposes of the present invention, rhizosphere competence can be assessed by using methods described in Example 1.

Another aspect the present invention relates to a method for enhancing resistance of plants to abiotic stresses which comprises contacting a *Trichoderma* strain with the plant or a plant seed under conditions effective for the *Trichoderma* strain to colonize the roots of the plant or a plant grown from the plant seed, thereby creating a plant-*Trichoderma* system. The plant or plant seed is grown under conditions effective to sustain the plant-*Trichoderma* system in a planting medium and to enhance resistance of plants to abiotic stresses, where the *Trichoderma* strain is selected from the group consisting of *Trichoderma atroviride* strain WW10TC4 (ATCC accession number PTA 9707), *Trichoderma harzianum* strain RR17Bc (ATCC accession number PTA 9708), *Trichoderma harzianum* strain F11Bab (ATCC accession number PTA 9709), and combinations thereof.

Plants derive numerous advantages from root colonization by *Trichoderma*. One important advantage is protection of plants against diseases by direct action of the *Trichoderma* strains on pathogenic microbes (Chet, I., "*Trichoderma*-Application, Mode of Action, and Potential as a Biocontrol Agent of Soilborne Plant Pathogenic Fungi," In *Innovative Approaches to Plant Disease Control*, pp. 137-160, I. Chet, ed., J. Wiley and Sons: New York (1987), which is hereby incorporated by reference in its entirety) or other deleterious soil microflora (Bakker et al., "Microbial Cyanide Production in the Rhizosphere in Relation to Potato Yield Reduction and *Pseudomonas* spp-Mediated Plant Growth-Stimulation," *Soil Biol Biochem* 19:451-457 (1987), which is hereby incorporated by reference in its entirety). *Trichoderma* offers protection against plant pathogens due to systemic induction of resistance. This permits plants to be protected at a point widely separated (temporally or spatially) from application of *Trichoderma* (Harman et al., "*Trichoderma* Species—Opportunistic, Avirulent Plant Symbionts," *Nature Microbiol Rev* 2:43-56, (2004), which is hereby incorporated by reference in its entirety). For example, through induced resistance, *Trichoderma* spp. can control foliar pathogens even when it is present only on the roots.

Another important advantage is that the *Trichoderma* strains of the present invention can provide protection against abiotic stress due to drought (water deficit), disease or other unfavorable plant growth conditions. Often times, plants may be cultivated in climates where the crop is exposed to many biotic and abiotic stresses such as plant diseases and drought. Drought conditions affect gene expression, amino acid profiles, and photosynthesis in plants thereby inducing stress. The majority of these responses may be delayed in plants treated with *Trichoderma* strains of the present invention. It may be possible to improve the tolerance of plants to drought by treating plants with *Trichoderma* strain of the present invention in the field. Plants with improved tolerance to drought, disease, and stress would be of benefit to the farmers by stabilizing crop yields and profitability.

The present invention also relates to a method for increasing nitrogen use efficacy in plants which comprises contacting a *Trichoderma* strain with the plant or a plant seed under conditions effective for the *Trichoderma* strain to colonize the roots of the plant or a plant grown from the plant seed, thereby creating a plant-*Trichoderma* system. The plant or plant seed is grown under conditions effective to sustain the plant-*Trichoderma* system in a planting medium and to increase nitrogen use efficacy in plants, where the *Trichoderma* strain is selected from the group consisting of *Trichoderma atroviride* strain WW10TC4 (ATCC accession number PTA 9707), *Trichoderma harzianum* strain RR17Bc (ATCC accession number PTA 9708), *Trichoderma harzianum* strain F11Bab (ATCC accession number PTA 9709), and combinations thereof.

*Trichoderma* strains may result in more and deeper roots and reduce the nitrogen requirement for plant growth presumably by enhancing nitrogen uptake. This capability can also be used to reduce nitrogen requirements for plant producers. These strains can also increase tolerance of plants to drought (Harman, G. E., "The Myths and Dogmas of Biocontrol. Changes in Perceptions Based on Research with *Trichoderma harzianum* T-22," *Plant Disease* 84:377-393 (2000), which is hereby incorporated by reference in its entirety).

To understand the relevance of the present invention, a consideration of the plant yield plateau is of importance. Plants generally respond to increasing nitrogen fertilizer levels with increased yield and growth up to a point and then the yield increase levels off; this is the yield plateau above which use of nitrogen fertilizer no longer increases yields. Planting seeds treated with *Trichoderma harzianum* has been shown to increase plant growth and productivity even under conditions of substantial nitrogen deficiency (Harman, G., "Myths and Dogmas of Biocontrol. Changes in Perceptions Derived from Research on *Trichoderma harzianum* T-22," *Plant Dis.* 84:377-393 (2000); Harman et al., "Enhancing Crop Performance and Pest Resistance with Genes from Biocontrol Fungi," In M. Vurro, J. Gressel, T. Butt, G. E. Harman, A. Pilgeram, R. J. St. Ledger and D. L. Nuss (eds.), *Enhancing Biocontrol Agents and Handling Risks* pp. 114-125. IOS Press, Amsterdam (2001); Harman et al., "*Trichoderma* Species—Opportunistic, Avirulent Plant Symbionts," *Nature Rev. Microbiol.* 2:43-56 (2004), which are hereby incorporated by reference in their entirety). Plants grown in the presence of the symbiotic biocontrol fungus frequently are greener and more vigorous (Harman, G., "Myths and Dogmas of Biocontrol. Changes in Perceptions Derived from Research on *Trichoderma harzianum* T-22," *Plant Dis.* 84:377-393 (2000), which is hereby incorporated by reference in its entirety). In the presence of *T. harzianum* this yield plateau was reached with 40-50% less nitrogen fertilizer than in its absence. Id.; Harman et al., "Enhancing Crop Performance and Pest Resistance with Genes from Biocontrol Fungi," In M. Vurro, J. Gressel, T. Butt, G. E. Harman, A. Pilgeram, R. J. St. Ledger and D. L. Nuss (eds.), *Enhancing Biocontrol Agents and Handling Risks* pp. 114-125. IOS Press, Amsterdam (2001), which are hereby incorporated by reference in their entirety. This means that nitrogen fertilizer rates could be reduced by this amount without a yield decrease. This has great potential both for decreasing evolution of $N_2O$ from soils, since less total fertilizer is applied, and since a greater percentage of the applied nitrogen must be taken up by the plant (the requirement for nitrogen in plant metabolism is not expected to be altered, so the only way to obtain the added N in the plant is via enhanced N use efficiency.

The present invention also relates to a method for reducing nitrous oxide emissions in air and leaching of nitrates into soil and water which comprises contacting a *Trichoderma* strain with the plant or a plant seed under conditions effective for the *Trichoderma* strain to colonize the roots of the plant or a plant grown from the plant seed, thereby creating a plant-*Trichoderma* system. The plant or plant seed is grown under conditions effective to sustain the plant-*Trichoderma* system in a planting medium and to reduce nitrous oxide emissions in air and leaching of nitrates into soil and water, where the *Trichoderma* strain is selected from the group consisting of *Trichoderma atroviride* strain WW10TC4 (ATCC accession number PTA 9707), *Trichoderma harzianum* strain RR17Bc (ATCC accession number PTA 9708), *Trichoderma harzianum* strain F11Bab (ATCC accession number PTA 9709), and combinations thereof.

Nitrous oxide gas is one of the gases responsible for the greenhouse effect and for the destruction of ozone layer. There are various sources of nitrous oxide emissions. Nitrogen fertilizer use is one of the major cause of $N_2O$ emissions. Soil microorganisms convert this nitrogen fertilizer into $N_2O$. Thus, a reduction in nitrogen fertilizer application would result in less $N_2O$ evolution, if there is no reduction in crop yield and growth. This requires an increase in nitrogen use efficiency by plants. Application of *Trichoderma* strains of the present invention to plants and crop would result in better efficiency of nitrogen uptake and use by plants, without reducing the plant biomass or yields. This would therefore indirectly reduce the application of nitrogen fertilizer to the planting medium and agricultural fields.

The present invention further relates to a method for enhanced sequestration of carbon from air which comprises contacting a *Trichoderma* strain with the plant or a plant seed under conditions effective for the *Trichoderma* strain to colonize the roots of the plant or a plant grown from the plant seed, thereby creating a plant-*Trichoderma* system. The plant or plant seed is grown under conditions effective to sustain the plant-*Trichoderma* system in a planting medium and to enhance sequestration of carbon from air, where the *Trichoderma* strain is selected from the group consisting of *Trichoderma atroviride* strain WW10TC4 (ATCC accession number PTA 9707), *Trichoderma harzianum* strain RR17Bc (ATCC accession number PTA 9708), *Trichoderma harzianum* strain F11Bab (ATCC accession number PTA 9709), and combinations thereof.

The *Trichoderma* strains of the present invention have abilities to increase plant biomass and growth. This can only occur if increased $CO_2$ sequestration from the atmosphere occurs since plants are formed of carbon compounds, including cellulose, hemicellulose, proteins, and other constituents. However, if plant biomass is reduced, then less $CO_2$ will be fixed into plant tissues by photosynthesis and both economic yield and global warming gases will be adversely affected.

Increase in plant biomass, can be made possible if there is a change in plant physiology that enhances photosynthesis. Indeed, the recent data indicates that these plant symbionts do alter the physiology of the plant. In proteomics studies, proteins involved in photosynthesis, respiration, and stress (both biotic and abiotic) were all up-regulated in the maize foliage in the presence of *T. harzianum*.

This is remarkable, since the beneficial fungus is located only on roots. It colonizes roots and induces the systemic changes. Thus, selection of proper strains and hosts is predicted to result in induced resistance to diseases, increased growth, and increased yield. With appropriate cultural practices, reduced greenhouse gases such as $CO_2$ and $N_2O$ can result through: (a) equal or greater yields of crops with reduced nitrogen fertilizer use through a shift of the position of the yield plateau to a lower level of N, thereby reducing $N_2O$ evolution from soil and (b) reduced carbon dioxide through greater photosynthetic activity of plants.

The methods of the present invention also include addition of supplemental source of nutrients to the plant-*Trichoderma* system. These include soil, water, urea, ammonium nitrate, sources providing nitrogen, phosphorous, potassium, calcium, magnesium, sulfur, and other micronutrients. In total, sixteen chemical elements are known to be important to a plant's growth and survival. The sixteen chemical elements are divided into two main groups: non-mineral and mineral. The non-mineral nutrients are hydrogen (H), oxygen (O), & carbon (C). These nutrients are found in the air and water. The other 13 are mineral nutrients. The 13 mineral nutrients, which come from the soil, are dissolved in water and absorbed through a plant's roots. There are not always enough of these nutrients in the soil for a plant to grow healthy. The mineral nutrients are further divided into two groups: macronutrients and micronutrients. The macronutrients are: N, P, S, K, Ca, Mg, Na and Si. The micronutrients are: Fe, Mn, Cu, Zn, Mo, B and Cl. Micronutrients are those elements essential for plant growth which are needed in only very small (micro) quantities. These nutrients and their benefits to plants would be well known to a person of skill in the art.

In practicing all aspects of the present invention, the organism may be prepared in a formulation containing organic or inorganic materials that aid in the delivery or contacting of the organism to the recipient plant or plant seed. Furthermore, in all aspects of the present invention described herein, contacting of the organism to a plant, seed, or other plant material may be carried out either simultaneously, before or after the introduction of the plant, seed, or other plant propagative material into the planting medium or area. The plant, seed or other plant material can be established (propagated) in any suitable planting medium, without limitations, as well as in any suitable environment, for example, a greenhouse or field environment. A person of skill in the art would readily be able to establish the requirements suitable for sustaining and/or propagating a plant.

The contacting of *Trichoderma* to the plant, plant seed, or planting medium can be carried out before, after or during the introduction of plant or plant seed to the planting medium. Regardless of the order in which contacting the organism to plant, seed, or other plant material is carried out, the following are all suitable methods in accord with the present invention for bringing the *Trichoderma* strains and plant material of choice in contact. Non-limiting examples of these methods include broadcast application, liquid or dry in-furrow application, spray application, irrigation, injection, dusting, pelleting, or coating of the plant or the plant seed or the planting medium with *Trichoderma* strain.

Beneficial organisms may be formulated or mixed to prepare granules, dusts, or liquid suspensions. These can be mixed directly into soils or planting mixes. The preparations are then mixed into the soil or planting mix volume for greenhouse applications or into the upper volume of field soil (Harman, G. E., "The Myths and Dogmas of Biocontrol. Changes in Perceptions Based on Research with *Trichoderma harzianum* T-22," *Plant Disease* 84:377-393 (2000), which is hereby incorporated by reference in its entirety). Equipment and procedures for such contacting are well known and used in various agricultural industries. Typical rates are 0.2 to 10 kg of product containing $10^7$ to $10^9$ colony forming units (cfu) per cubic meter of planting mix or soil.

Contacting can also be done by liquid application (drenches) for greenhouse or nursery soils and soil mixes. Liquid suspensions of the beneficial microorganisms can be prepared by mixing dry powder formulations into water or another carrier, including fertilizer solutions, or by diluting a liquid formulation containing the organism in water or other aqueous solutions, including those containing fertilizers. In either case, the formulation may include other organic or non-organic additives to aid in dissolving or applying the mixture. Solutions can then be used to water planting mixes either prior to planting or else when plants are actively growing, such as by field irrigation. Typically, 10 to 400 ml of product (usually 150/inn or smaller in particle size) containing $10^7$ to $10^9$ cfu are mixed with 100 L of water for such applications.

Seeds are commonly treated using slurry, film-coating or pelleting by processes well known in the trade (Harman et al., "Factors Affecting *Trichoderma hamatum* Applied to Seeds As a Biocontrol Agent," *Phytopathology* 71:569-572 (1981); Taylor et al., "Concepts and Technologies of Selected Seed Treatments," *Ann. Rev. Phytopathol.* 28: 321-339 (1990), which are hereby incorporated by reference in their entirety). The beneficial microbial agents of the present invention can effectively be added to any such treatment, providing that the formulations do not contain materials injurious to the beneficial organism. Depending on the organism in question, this may include chemical fungicides. Typically, powder or liquid formulations ($10^7$ to $10^{10}$ cfu/g) of the organism are suspended in aqueous suspensions to give a bioactive level of the organism. The liquid typically contains adhesives and other materials to provide a good level of coverage of the seeds and may also improve its shape for planting or its cosmetic appeal.

Contacting can also be accomplished by dry powders containing beneficial organisms can be applied as a dust to roots, bulbs or seeds. Generally fine powders (usually 250/inn or smaller) are dusted onto seeds, bulbs or roots to the maximum carrying powder (i.e., until no more powder will adhere to the treated surface). Such powders typically contain $10^7$ to $10^9$ cfu/g.

Liquid suspensions of products may be injected under pressure into the root zone of appropriate plants through a hollow tube located at the depth desired by the application. Equipment for such application is well known in the horticulture industry. Alternatively, suspensions or powders containing appropriate organisms can be applied into wells or other aqueous environments in the soil. Liquid suspensions of products may be prepared as described above for preparing drenches. Such materials may be added to the furrow into which seeds are planted or small plants are transplanted. Equipment for such applications is widely used in the agricultural industry. Typical rates of application are 0.5 to 10 kg of product ($10^7$ to $10^9$ cfu/g) per hectare of field.

Granules, as described above, can be broadcast onto soil surfaces that contain growing plants, to soil at the time of planting, or onto soils into which seeds or plants will be planted. Typical rates range from 1 to 500 kg of product containing $10^7$ to $10^9$ cfu/g depending upon the plants to be treated and the goals of the treatment. Alternatively, spray solutions can be prepared as described above, and applied to give similar rates (Harman, G. E., "The Myths and Dogmas of Biocontrol. Changes in Perceptions Based on Research with *Trichoderma harzianum* T-22," *Plant Disease* 84:377-393 (2000); Lo et al., "Biological Control of Turfgrass Diseases with a Rhizosphere Competent Strain of *Trichoderma harzianum,*" *Plant Disease* 80:736-741 (1996); Lo et al., "Improved Biocontrol Efficacy of *Trichoderma harzianum* 1295-22 for Foliar Phases of Turf Diseases By Use of Spray Applications," *Plant Disease* 81:1132-1138 (1997), which are hereby incorporated by reference in their entirety).

For the purposes of the present invention, all methods which describe application, contacting or introduction of *Trichoderma* strains to the plant, seeds, or plant propagative materials are designed to accomplish the same purpose, i.e., to provide a means of application that will result in effective colonization of the root by the beneficial organism (Harman et al., "Potential and Existing Uses of *Trichoderma* and *Gliocladium* For Plant Disease Control and Plant Growth Enhancement," In *Trichoderma and Gliocladium*, Harman et al., eds., Vol. 2, London:Taylor and Francis (1998), which is hereby incorporated by reference in its entirety).

The methods and the strains of the present invention can be utilized with a wide variety of plants and their seeds. Suitable plants and their seeds include ferns, conifers, monocots, and dicots. Suitable plants and their seeds to which the *Trichoderma* strains of the present invention can be applied include all varieties of dicots and monocots, including crop plants and ornamental plants. More particularly, useful crop plants and their seeds include, without limitation: alfalfa, rice, wheat, barley, oats, rye, cotton, sorghum, sunflower, peanut, potato, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, maize, clover, and sugarcane. Examples of suitable ornamental plants and their seeds are, without limitation, *Arabidopsis thaliana, Saintpaulia*, petunia, pelargonium, poinsettia, chrysanthemum, carnation, zinnia, roses, snapdragon, geranium, zinnia, lily, daylily, Echinacea, dahlia, hosta, tulip, daffodil, peony, phlox, herbs, ornamental shrubs, ornamental grasses, switchgrass, and turfgrass.

EXAMPLES

Example 1

Rhizosphere Competence and Enhanced Root Development

The revolution that has occurred in the understanding of *Trichoderma*-plant interactions has led to screening systems for identification of better and improved strains with desirable properties. There could be several criteria for selection of better strains, for example, the identification of rhizosphere competence. Rhizosphere competence can be defined as the abilities of strains to efficiently colonize roots, to grow with and to colonize the entire root system. This permits long-term, at least season long, effects on plants.

Rhizosphere competence can readily be assessed, for example, by the methods described in Sivan et al. "Improved Rhizosphere Competence in a Protoplast Fusion Progeny of *Trichoderma harzianum*," *J. Gen. Microbiol.* 137:23-29 (1991), which is hereby incorporated by reference in its entirety. For the purposes of the present invention, rhizosphere competence can be assessed by the following method: seeds of any convenient plant species (cotton, beans or maize are preferred) are treated with the *Trichoderma* strain of interest by application of conidia of the strain suspended in water or water containing an adhesive such as carboxymethyl cellulose or other material common to the seed coating trade. The suspension should contain $10^7$ to $10^8$ conidia/ml. Seeds are then planted in soil or commercial planting mix at a moisture level conducive to seed germination. The seedlings are grown from treated or untreated seeds without further watering in a closed system until roots are 10-15 cm in length. A useful arrangement, essentially as in Sivan et al. "Improved Rhizosphere Competence in a Protoplast Fusion Progeny of *Trichoderma harzianum*," *J. Gen. Microbiol.* 137:23-29 (1991), which is hereby incorporated by reference in its entirety, for such assays is to grow individual seedlings in a 2.5 cm diameter split plastic (PVC) pipe 15 cm long. The pipe halves are held together with rubber bands or tape and filled with soil or planting medium. One seed is planted in the soil at the top of the pipe and seedlings grown until they reach the desired size. Pipes containing seedlings are contained within a closed container to prevent evaporation of moisture and with a layer of moist planting medium at the bottom of the container. This arrangement provides a system that avoids the need for watering of the soil. Watering may carry conidia away from treated seeds into the planting mix into the lower soil volume, which must avoided. When seedlings are of the desired size, the two halves of the pipe and separated and the root carefully removed from the soil or planting medium. Alternatively, seedlings can be grown in an appropriate soil without watering and then carefully removed. The distal 1 cm end of the root is excised and either plated directly or else washed to remove spores. The excised root tips or spore washings are then plated onto an appropriate medium for detection of *Trichoderma*. A preferred medium is acid potato dextrose agar made according to the manufacturer's directions (DIFCO, Detroit, Mich.) and containing 1% of the colony-restricting agent Igepal Co630 (ALLTECH ASSOCIATES, Deerfield, Ill.). The acidic nature of the medium prevents growth of most interfering bacteria and the colony restricting agent assists in enumeration of colony numbers. For this assay, rhizosphere competent strain is defined as one that, following application as a seed treatment, results in colonization of root tips of at least 80% of seedlings. Other assays could also be used or developed for assessing the rhizosphere compliance of the strains. It should be noted that the ability of *Trichoderma* to colonize roots is rare (Chao et al., "Colonization of the Rhizosphere by Biological Control Agents Applied to Seeds," *Phytopathology* 76:60-65 (1986), which is hereby incorporated by reference in its entirety), and occurs only with a few strains, so this definition of rhizosphere competent strain excludes most strains of *Trichoderma*.

The examples in the present invention use seed treatment to deliver effective *Trichoderma* strains to plants, after which rhizosphere competent strains then colonize roots. It will be appreciated that any method of delivery of the *Trichoderma* strains to soil, including drenching, in-furrow applications, broadcast applications to soil or application of granular materials to the planting mix, will result in colonization of roots by effective strains. It will also be appreciated that natural soils, synthetic potting mixes, rock wool, or any other planting mix capable of supporting plant growth can be used.

Enhanced root proliferation is a very important component of the present invention. In every case, it is accompanied by an increase in shoot growth as well, so an increase in shoot growth is a good indicator also of root development. Enhanced root development is essential to improved nitrogen use efficiency, since the development of enhanced root systems is essential to intercept and take up nitrogen fertilizer. It also is important for attributes such as drought tolerance (Harman, G., "Myths and Dogmas of Biocontrol. Changes in Perceptions Derived from Research on *Trichoderma Harzianum* T-22," *Plant Dis.* 84:377-393 (2000), which is hereby incorporated by reference in its entirety) and bioremediation of toxic materials in soils (Adams et al., "*Trichoderma harzianum* Rifai 1295-22 Mediates Growth Promotion of Crack Willow (*Salix Fragilis*) Saplings in Both Clean and Metal-Contaminated Soil," *Microbial. Ecol.* 54:306-313 (2007); Harman et al., "Uses of *Trichoderma* spp. to Remediate Soil and Water Pollution," *Adv. Appl. Microbiol.* 56:313-330 (2004), which is hereby incorporated by reference in its entirety).

Example 2

Selection of Improved Strains

Various strains of *Trichoderma* were selected and tested for rhizosphere competence. All of the strains described in the present application were prepared with a process of asexual hybridization using protoplast fusion (Stasz et al., "Nonparental Progeny Resulting from Protoplast Fusion in *Trichoderma* in the Absence of Parasexuality," *Exp. Mycol.* 14:145-159 (1990), which is hereby incorporated by reference in its entirety). To ensure rhizosphere competence, the distal root isolation procedure, as described in Example 1, was used to identify subisolates. As noted elsewhere, these have some instability and are sectored. Several different sectors were isolated and tested. The number system for the strains is important. The first letter or letters indicates the specific protoplast fusion that was conducted and the number immediately following described the order in which the specific progeny was picked. Each different set of letters indicates a different set of parents. While the original species were known, these indicators now are largely meaningless. At the time of U.S. Pat. No. 5,260,213 to Harman et al., which is hereby incorporated by reference in its entirety, there were nine species groups based on fungal morphological characteristics. Now there are more than 100 recognized species based on sequences of elongation factor genes and ITS spacer regions, as defined on the International *Trichoderma* taxonomy website, where species are now defined by sequence bar codes.

After the first letter and number designations, the sectors that were picked were given letters. If the letter is a capital, this means that the selection was made at the time the isolates were first obtained, and the small letter designations are those that were picked in the most recent set of selections. For example, RR17Bc indicates that the strain arose from fusion RR, was the 17$^{th}$ isolate picked, and that in the original selection, sector B was isolated. Further, after screening for rhizosphere competence, another sector (c) was selected (Shoresh et al., "The Molecular Basis of Maize Responses to *Trichoderma harzianum* T22 innoculation: A Proteomic Approach," *Plant Physiol.* 147:2147-2163 (2008), which is hereby incorporated by reference in its entirety).

Strains were first chosen for their abilities to enhance growth of cucumbers or wheat, as shown below. For these experiments, seeds were treated with a *Trichoderma* preparation containing about $1 \times 10^{10}$ colony forming units (cfu) per g. A weighed quantity (100 ng) was added to 5 ml of water. Twenty μl of this suspension was used to treat 1 g of seeds to give around $4 \times 10^6$ cfu/g g of seeds. Treated or untreated seeds were planted in a standard peat-vermiculite planting mix in 4 inch plastic pots. There were five seeds planted per pot and each pot was considered a replicate. There were five replicates arranged in the greenhouse in a randomized complete block design and values presented are averages of each replicate +/− the standard deviation. The results are shown in FIG. 1.

Figure 2:
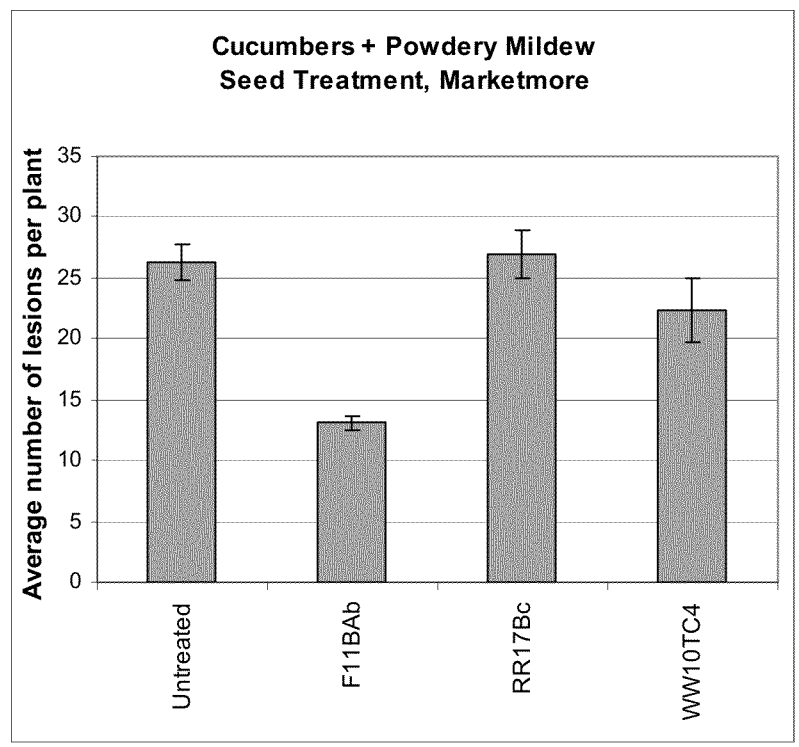
FIG. 2 shows the reduction of powdery mildew on cucumber foliage treated in accordance with the present invention.

Based on data over both wheat and cucumber, *Trichoderma* strains RR17Bc and WW10TC4 were chosen for further testing. Similarly, strains were also tested for their abilities to increase resistance to disease. The model system was powdery mildew on cucumber. FIG. 2 shows the reduction of powdery mildew on cucumber foliage. Based on this testing, F11Bab was added to list of elite strains.

Sequences were isolated from these three strains and species assessment was conducted based on the criteria in International *Trichoderma* taxonomy website. Strains RR17Bc and F11Bab are in the species *T. harzianum* while WW10TC4 is a strain of *T. atroviride*.

It is important to note that even closely related sister strains can give different reactions, so selection based on plant performance is important.

It also is important to note that greater growth responses frequently or usually occur when plants are under biotic or abiotic stresses than when they are growing under optimal conditions. Suboptimal light conditions may even be sufficient to give greater differential growth in the presence of the endophytic strains that are the subject of the present invention than under optimal light conditions. Thus, even with supplemental lighting, variable results may be seen at different times of the year or other environmental variables.

Example 3

Increase in Growth of Wheat

Figure 3:
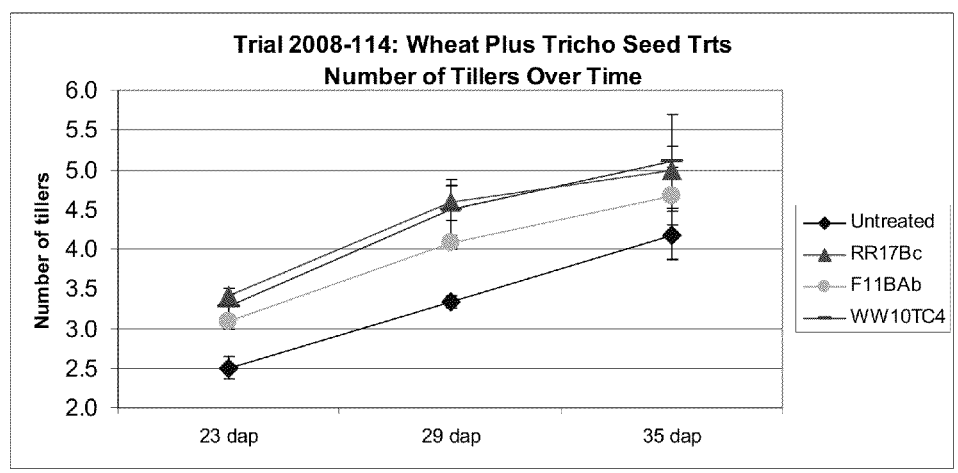
FIG. 3 shows the tillering over time in spring wheat treated in accordance with the present invention.
Figure 4:
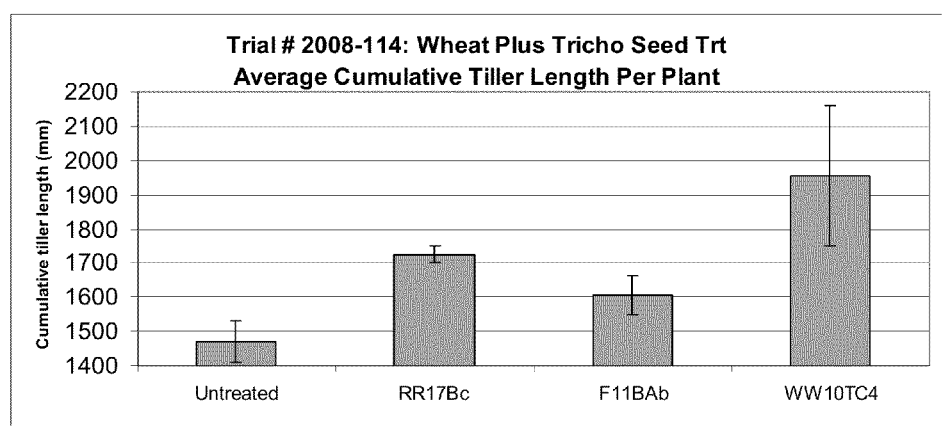
FIG. 4 shows the cumulative tiller length in wheat treated in accordance with the present invention.

Increased biomass of wheat may be expressed as numbers of tillers (also known as side shoots) that are produced. As the wheat plant grows, it forms tillers that each provides an additional head of grain. Thus, for example, if the wheat plant sequesters more carbon, this ought to be expressed as additional tillering. These experiments, which measured the number of tillers (FIG. 3), were conducted in a greenhouse using seeds of spring wheat variety Glenn which were treated following the protocol described in Example 1. Assuming that tiller lengths are similar across treatments, the total cumulative tiller length ought to be greater in strains that increase tiller number. This data is shown in FIG. 4. Data is shown with the standard deviation. As can be seen, all of the strains tested increased total tiller length relative to the control.

Data obtained shows that the three strains increase yield and tillering in wheat. These data indicate that (a) the new strains will increase yields of wheat, (b) that rooting will be enhanced along with shoot growth, thus permitting lower nitrogen fertilizer usage rates without yield reduction and (c) that carbon dioxide must be sequestered at a greater level to account for the increase in stem length and weight.

Again, as mentioned in the previous example, the level of increased growth in the presence of the strains will be affected by an biotic or abiotic stresses during the growing period.

Example 4

Increase in Nitrogen Fertilizer Use Efficiency

The ability of the new strains to enhance nitrogen use efficiency in wheat was evaluated. Experiments were conducted as nitrogen rate ranging trials in large pots (4 L volume) to avoid root binding in smaller pots. Trials were conducted in a sandy loam:vermiculite:peat potting mix, to which adequate levels of minor nutrients and P and K were added, and a variable amount of nitrogen (N), added as urea, was added to give a range of N concentrations that varied from 40 to 320 lb/N/acre equivalent. These nitrogen rate-ranging experiments are the only way to fully define the yield/nitrogen uptake effects of added *Trichoderma*. When seedlings first emerged, a substantial stunting was noted in the presence of *Trichoderma* at concentrations of 160 lb/acre and above, but the same stunting was evident in the absence of *Trichoderma* only above 240 lb N/acre. This indicates that the *Trichoderma* strains were increasing N uptake, and that high levels of N were toxic. Since the toxicity occurred at lower concentrations in the presence of the *Trichoderma* strains, this data suggests that the strains were indeed increasing uptake and that toxic levels were reached at lower N concentrations in the presence than in the absence of *Trichoderma*. This has importance in other examples that follow.

Figure 5:
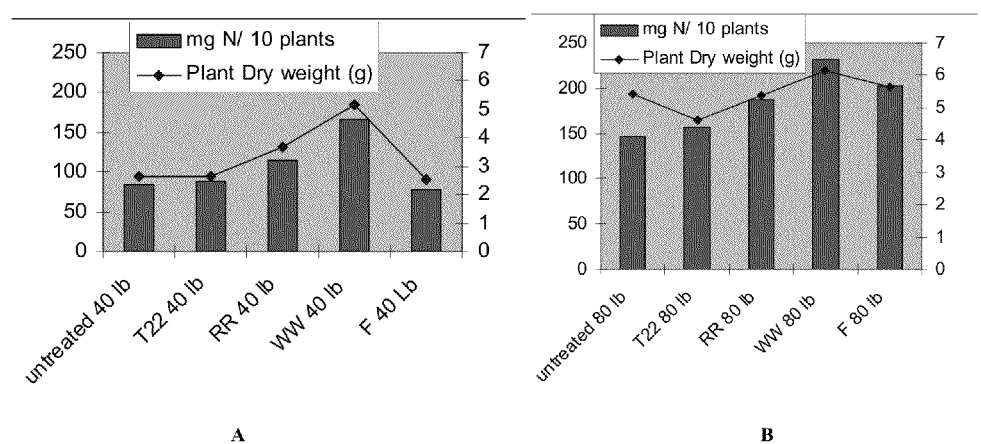
FIGS. 5A-B show the relationship between plant weight and N level of wheat plants grown at 40 lb (FIG. 5A) and 80 lb/acre (FIG. 5B) equivalent of N.

However, at N levels of 80 lb and below, as plants first emerged from the soil, there was no difference in plants sizes. However, by 49 days, at the time of emergence of heads, there was a difference in plants that grew from untreated or the different *Trichoderma* strains in soils to which N at 40 (FIG. 5A) or 80 lb of N (FIG. 5B) were added. The plant heights were first measured, where the differences were significant at the two lower N rates. Plants were then destructively sampled from one replicate of the trials, and total plant weight, N levels, as well as levels of other nutrients was measured.

Figure 6:
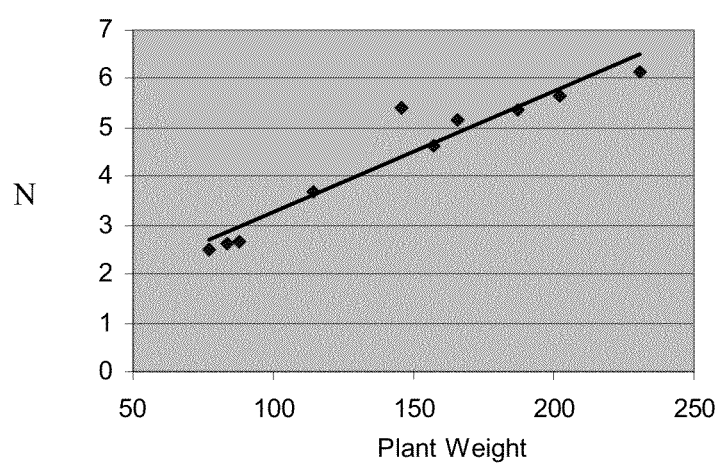
FIG. 6 shows the regression of N level in wheat plants and plant size.

The growth of wheat was very tightly correlated with N level in these experiments at this N range. FIG. 6 provides the regression between N content of the wheat and plant weight.

These data clearly show that the level of N is very tightly correlated with plant weight and that *Trichoderma* strains, especially strains RR17Bc and WW10TC4, are highly effective in enhancing N uptake from soil. Since plant weights are tightly correlated with N levels it is likely that one principal effect of the enhancement in plant growth is due to enhanced N uptake. However, even when N is sufficient in soil, there may still be an increase in plant growth due to the enhanced N uptake level since the greater efficiency may increase N levels to higher levels than otherwise.

Thus, the data demonstrate: 1) *Trichoderma* strains, especially RR17Bc and WW10TC4, are very efficient in enhancing the uptake of N from nitrogen-poor soils. At 40 lb N, there was about 2× as much N in plants in the presence of WW10TC4 than occurred with no *Trichoderma* seed treatment; 2) that much of the enhanced growth of wheat by *Trichoderma*, and probably other crops, is due to this enhanced nitrogen level in crops, which results from more efficient N fertilizer uptake; 3) seed treatment with the best strain, *T. atroviride* WW10TC4, in soils at 40 lb N/acre equivalent resulted in plants that were about the same size as plants grown from nontreated seeds at 80 lb N/acre—thus, growth with 50% less added N gave similar results as the higher rate without it; 4) plant growth at 80 lb N with WW10TC4 was 50% greater than with control plants—N probably is still somewhat limiting even at the high rate, but there probably are two separate mechanisms operating—the first is a growth promotion phenomenon that is a general effect of the strains and the second is the increase in N use efficiency; 5) the new strains *T. atroviride* WW10TC4 and *T. harzianum* RR17Bc gave substantial improvements in performance over the old standard strain *T. harzianum* T22; and 6) care must be exercised not to use the *Trichoderma* strains that increase N uptake at high N application, since the combination of enhanced nitrogen uptake in high N levels soils can result in toxicity to the plants.

Example 5

Improved Nitrogen Use Efficiency in Rice in Field Experiments

For some experiments, seeds were treated with conida of strains F11Bab and RR17Bc, or else roots were dipped in these strains at the time of transplanting. The trial was conducted with lowland rice. The plots were conducted in a randomized complete block design with four replicates. Fertilizer was added at the normal rate of nitrogen or at the half rate of nitrogen; a no fertilizer check was also included with the beneficial organisms.

TABLE 1

Yields of Lowland Rice upon *Trichoderma* Treatment.

| Treatment* | Yield (tons/ha) | Yield (tons/ha) |
|---|---|---|
| No fertilizer check | 5.78 | — |
| | Full Rate N | ½ Rate N |
| No *Trichoderma* | 7.29 | 6.55 |
| ST F11Bab (ATCC PTA-9709) | 7.28 (0%) | 7.77 (+18%) |
| ST RR17Bc (ATCC PTA-9708) | 6.79 (−7%) | 7.55 (+15%) |
| RD F11Bab (ATCC PTA-9709) | 6.79 (−7%) | 8.52 (+31%) |
| RD RR17Bc (ATCC PTA-9708) | 7.29 (0%) | 7.05 (+8%) |

*ST refers to application by a seed treatment, while RD refers to application to rice seedling roots at the time of transplanting.

The yield at no fertilizer check was significantly less than the yield at the full rate of fertilizer, and lower by about 13% than the no-*Trichoderma* ½ rate yield. At the full rate of N, there was no difference between the yields when *Trichoderma* was applied or not applied, and sometimes, the yields where *Trichoderma* was applied were lower. However, with the beneficial organisms at the ½ rate N, yields were at least equal to the same treatment at the full rate of N, and 15-30% greater than the yield at half rate N without *Trichoderma*. Yields with the strains at the half rate were numerically higher than the yields with the same treatment at the full rate of N.

Thus, the hypothesized result, i.e., that yields at half rate of N were improved and not less than the full rate, was obtained.

Example 6

Ability to Improve Resistance to Drought

The strains also have abilities to overcome abiotic stresses. Rice seeds were treated with F11Bab (ATCC PTA-9709), and planted in a rice paddy. During the course of the trial, after plants emerged, the dike broke and the plants were left without water. The plants without F11Bab all died from drought and had no harvest, but a normal harvest was obtained in the presence of the beneficial fungus.

Example 7

Improved Stand and Vigor of Winter Wheat Seedlings

A field trial with winter wheat was planted near Phelps, N.Y., in October, 2009. The seeds used were treated with the fungicide Dividend™ which a standard seed protectant. The seeds were treated with the strains described in the present invention or not treated, in a randomized replicated field plot. In November, stands in three feet of row were counted in each replicate of each treatment and visual vigor ratings were made on 1-10 scale, with 10 being highly vigorous. The results are shown in Table 2. Numbers in the brackets are standard deviations around the mean.

TABLE 2

Stand Count of Wheat after *Trichoderma* Treatment.

Stand counts/seedlings 3 feet of row

| Strain used for seed treatment | Stand counts (S.D.) |
|---|---|
| F11Bab | 60 (1.5) |
| WW10TC4 | 58 (3.8) |
| RR17Bc | 55 (3.2) |
| Untreated | 48 (2.2) |

Vigor Ratings

| Seed treatment | Vigor rating (S.D.) |
|---|---|
| F11Bab | 8.7 (0.2) |
| WW10TC4 | 8.3 (0.27) |
| RR17Bc | 8.1 (0.23) |
| Untreated | 7.9 (0.23) |

These data demonstrate the treatment of wheat with the *Trichoderma* strains increased stands, even when applied over a standard, quality fungicide and that the plots were more vigorous in the fall. This is the first requirement for increased plant stands.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for enhancing growth of plants comprising:
   contacting a *Trichoderma* strain with a plant or a plant seed under conditions effective for the *Trichoderma* strain to colonize the roots of the plant or a plant grown from the plant seed, thereby creating a plant-*Trichoderma* system and
   growing the plant or plant seed under conditions effective to sustain the plant-*Trichoderma* system in a planting medium and to enhance plant growth, wherein the *Trichoderma* strain is *Trichoderma atroviride* strain WW10TC4 (ATCC accession number PTA 9707).

2. The method according to claim 1 further comprising:
   adding a supplemental source of nutrients to the plant-*Trichoderma* system.

3. The method according to claim 2, wherein the nutrients are selected from the group consisting of soil, water, urea, ammonium nitrate, and sources providing nitrogen, phosphorous, potassium, calcium, magnesium, sulfur, and/or other micronutrients.

4. The method according to claim 1, wherein the *Trichoderma* strain is provided as a granule, dust, powder, slurry, film, liquid suspension, or combinations thereof.

5. The method according to claim 1, wherein said contacting is carried out by broadcast application, liquid or dry in-furrow application, spray application, irrigation, injection, dusting, pelleting, or coating of the plant or the plant seed or the planting medium with *Trichoderma* strain.

6. The method according to claim 1, wherein said contacting is carried out before the plant or the plant seed is introduced to the planting medium.

7. The method according to claim 1, wherein said contacting is carried out after the plant or the plant seed is introduced to the planting medium.

8. The method according to claim 1, wherein the plant or plant seed is a crop plant selected from the group consisting of alfalfa, rice, wheat, barley, oats, rye, cotton, sorghum, sunflower, peanut, potato, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, maize, clover, and sugarcane.

9. The method according to claim 1, wherein the plant or plant seed is an ornamental plant selected from the group consisting of *Arabidopsis thaliana, Saintpaulia*, petunia, pelargonium, poinsettia, chrysanthemum, carnation, zinnia, roses, snapdragon, geranium, zinnia, lily, daylily, Echinacea, dahlia, hosta, tulip, daffodil, peony, phlox, herbs, ornamental shrubs, ornamental grasses, switchgrass, and turfgrass.

10. The method according to claim 1, wherein the *Trichoderma* strain further comprises *Trichoderma harzianum* strain F11Bab (ATCC accession number PTA 9709).

11. The method according to claim 1, wherein the plant growth enhancement is in the form of greater root mass, greater depth of rooting, greater shoot mass, greater length of shoots, increased leaf greenness, increased yields, and improved stand and vigor.

12. A method for enhancing resistance of plants to abiotic stresses comprising:
    contacting a *Trichoderma* strain with the plant or a plant seed under conditions effective for the *Trichoderma* strain to colonize the roots of the plant or a plant grown from the plant seed, thereby creating a plant-*Trichoderma* system and
    growing the plant or plant seed under conditions effective to sustain the plant-*Trichoderma* system in a planting medium and to enhance resistance of plants to abiotic stresses, wherein the *Trichoderma* strain is *Trichoderma atroviride* strain WW10TC4 (ATCC accession number PTA 9707).

13. A method for increasing nitrogen use efficacy in plants comprising:
    contacting a *Trichoderma* strain with the plant or a plant seed under conditions effective for the *Trichoderma* strain to colonize the roots of the plant or a plant grown from the plant seed, thereby creating a plant-*Trichoderma* system and
    growing the plant or plant seed under conditions effective to sustain the plant-*Trichoderma* system in a planting medium and to increase nitrogen use efficacy in plants, wherein the *Trichoderma* strain is *Trichoderma atroviride* strain WW10TC4 (ATCC accession number PTA 9707).

14. A method for reducing nitrous oxide emissions in air and leaching of nitrates into soil and water, said method comprising:
    contacting a *Trichoderma* strain with the plant or a plant seed under conditions effective for the *Trichoderma* strain to colonize the roots of the plant or a plant grown from the plant seed, thereby creating a plant-*Trichoderma* system and
    growing the plant or plant seed under conditions effective to sustain the plant-*Trichoderma* system in a planting medium and to reduce nitrous oxide emissions in air and leaching of nitrates into soil and water, wherein the *Trichoderma* strain is *Trichoderma atroviride* strain WW10TC4 (ATCC accession number PTA 9707).

15. A method for enhancing sequestration of carbon from air comprising:
    contacting a *Trichoderma* strain with the plant or a plant seed under conditions effective for the *Trichoderma* strain to colonize the roots of the plant or a plant grown from the plant seed, thereby creating a plant-*Trichoderma* system and growing the plant or plant seed under conditions effective to sustain the plant-*Trichoderma* system in a planting medium and to enhance sequestration of carbon from air, wherein the *Trichoderma* strain is *Trichoderma atroviride* strain WW10TC4 (ATCC accession number PTA 9707).

16. An isolated *Trichoderma atroviride* strain WW10TC4 deposited with ATCC under accession number PTA 9707.

17. The isolated *Trichoderma atroviride* strain WW10TC4 according to claim 16 which is biologically pure.

18. A plant-*Trichoderma* system comprising:
a plant or a plant seed and
a *Trichoderma* strain which is *Trichoderma atroviride* strain WW10TC4 (ATCC accession number PTA 9707).

19. The plant-*Trichoderma* system according to claim 18, wherein the *Trichoderma* strain further comprises *Trichoderma harzianum* strain F11Bab (ATCC accession number PTA 9709).

20. The isolated *Trichoderma harzianum* strain WW10TC4 according to claim 16 in combination with a *Trichoderma harzianum* strain F11Bab (ATCC accession number PTA 9709).

* * * * *